United States Patent
Irion et al.

(10) Patent No.: US 6,468,202 B1
(45) Date of Patent: Oct. 22, 2002

(54) ENDOSCOPE ADAPTER WHICH CAN BE DETECTED USING COMPUTER ASSISTED SURGERY

(75) Inventors: Klaus M. Irion, Liptingen; Clemens Rebholz, Uhldingen-Mühlhofen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/669,640

(22) Filed: Sep. 26, 2000

Related U.S. Application Data (63) Continuation of application No. PCT/EP99/02021, filed on Mar. 25, 1999.

(30) Foreign Application Priority Data

Mar. 26, 1998 (DE) .......................................... 198 13 383

(51) Int. Cl.⁷ ................................................. A61B 19/00
(52) U.S. Cl. ........................ 600/117; 600/112; 600/138; 606/130
(58) Field of Search ................................ 600/112, 117, 600/138, 417, 429; 606/130

(56) References Cited

U.S. PATENT DOCUMENTS

| | | |
|---|---|---|
| 4,478,212 A | 10/1984 | Asano |
| 4,807,594 A | 2/1989 | Chatenever |
| 5,517,990 A | 5/1996 | Kalfas et al. ............. 128/653.1 |
| 5,591,119 A * | 1/1997 | Adair .......................... 600/112 |
| 5,617,857 A | 4/1997 | Chader et al. ........... 128/653.1 |
| 5,647,373 A * | 7/1997 | Paltieli ........................ 600/567 |
| 6,021,343 A * | 2/2000 | Foley et al. ................. 600/429 |

FOREIGN PATENT DOCUMENTS

| | | |
|---|---|---|
| DE | 19813383 A1 | 3/1998 |
| EP | 0672389 A2 | 3/1995 |

OTHER PUBLICATIONS

P. Cinquin et al; *Computer Assisted Medical Interventions, Engineering in Medicine and Biology*; May/Jun. 1995; 10 pages.

* cited by examiner

Primary Examiner—John Mulcahy
(74) Attorney, Agent, or Firm—St. Onge Steward Johnston & Reens LLC (57) ABSTRACT

An apparatus is provided comprising a transmitter unit for detecting the position of a medical instrument with the aid of a CAS system, wherein the apparatus comprises the transmitter unit at a fixed position and wherein the medical instrument is attachable to the apparatus. To allow simple assembly and disassembly, the apparatus is formed as an adapter. A reception coupling is provided on one first side of the adapter at which the adapter can be releasably, however mechanically fixed and simply coupled to a predetermined coupling location on the medical instrument.

26 Claims, 5 Drawing Sheets

ENDOSCOPE ADAPTER WHICH CAN BE DETECTED USING COMPUTER ASSISTED SURGERY

CROSSREFERENCE OF PENDING APPLICATION

This application is a continuation of pending International Application PCT/EP99/02021 filed on Mar. 25, 1999.

BACKGROUND OF THE INVENTION

The invention relates to an apparatus comprising a transmitter unit with which the position of a medical instrument can be determined with the aid of a CAS system. The apparatus comprises the transmitter unit at a fixed location and the apparatus can be attached to the medical instrument.

Such an apparatus is disclosed in the article by Cinquin, P. et al.: "Computer Assisted Medical Intervention", IEEE Engineering in Medicine and Biology, May/June 1995, pages 256 to 263.

So-called CAS systems (computer assisted surgery) are increasingly used in various operations, for example in neurosurgery, spinal surgery and surgery relating to the throat, nose and ears. Such systems are also indicated with the abbreviation CAMI=computer assisted medical intervention. These CAS systems consist at least of a position sensor unit which detects the position and/or the direction of an instrument, for example an endoscope, and transmits this information to an image processing unit in which data in the form of CT, MR and/or ultrasound images of the body region to the be treated are present in three dimensionals. After reference markings are correlated with three dimensional image data corresponding to the original position data, a correct position determination of instruments is possible in the image data set. The operator thus has the possibility to orient himself during an operation on the basis of image data reproduced on a monitor. A prerequisite for precise localization, apart from the accuracy of the position detection, is especially the geometric invariance of the body structure from the time the image data is taken until the time of the operation. Thus this method is especially suitable for operations in which rigid body structures are involved and the shifting capability of soft tissue is small, i.e. for operations on the skull, on the spine or the sinuses.

The position detection in the above-mentioned apparatus is effected by means of several radiating diode or position elements, whose signals can be detected from remote cameras and supplied to a computer.

The position of the diodes and thus the position of the instrument connected directly thereto is determined with the triangulation method in the computer. The transmitter unit must be connected at a fixed position with the instrument, for example an endoscope whose position is to be determined. This connection must remain invariable during the operation. In the abovementioned apparatus, a total of six diodes are arranged on an approximately T-shaped or sword-shaped bulky and voluminous component, which is attached in the region of a shaft of the respective instrument, namely either on the shaft of an endoscope or on the shaft of a borer. The apparatus can be positioned along the shaft and its position fixed by screws employing a sleeve covering the shaft.

A disadvantage of the known apparatus is that the mounting procedure and the change of the transmitter unit to another instrument, for example to another endoscope, are very time consuming and complicated. Such a change is only possible with considerable effort, especially under clinical conditions during an operation and under the requirements on sterility.

Several instruments are often employed in certain operations and in the course of an operation it is necessary to re-use an instrument employed at the beginning, which in the meantime has been set aside. For example, if the instrument is an endoscope with a so-called straight view, then this endoscope can be used at the beginning of the operation to approach an operation site by inserting along the endoscope axis, for example through the nose to a site in the sinus cavity. Should an operation then be carried out on a tumor located to the side of the operation site, the endoscope with the straight view is replaced with an endoscope having a side view.

Should the operation area be inspected again for remaining objects at the end of the operation, the initial endoscope with the straight view is required again. In addition, the change from or to a passive instrument is also frequently necessary, for example when a trocar with an obturator is to be inserted, i.e. without viewing.

Each instrument must be provided with numerous, at least three, transmitters in order to be able to determine the position of the respective instrument. This is complicated and expensive. Consequently, numerous coupling and decoupling procedures of the components of the medical instruments must be made during an operation. The components coupled to an endoscope are mainly cameras, which are connected to a processor unit and a monitor with cables. The problem of contamination of the sterile instruments arises due to the non-sterile components, such as cameras or the like.

The object of the present invention is therefore to provide an improved apparatus of the above-mentioned type, where the position detection of the respective instrument is carried out precisely and with little effort and where the coupling and decoupling between parts of the medical instruments and the CAS system are carried out in simple, rapid and reliable manner under sterile conditions.

SUMMARY OF THE INVENTION

According to the present invention, the apparatus is configured as an adapter comprising a reception coupling on a first side, with which it can simply be coupled to a predetermined connecting location on the medical instrument in releasable, but mechanically fixed manner.

It is no longer necessary to provide a transmitter unit on each instrument, but only necessary to couple the adapter to the instrument to be detected, which can be accomplished by a simple procedure. The adapter need only be placed upon the corresponding connecting location present on the instrument and coupled thereto, which can be performed in a clip-on manner. The adapter can be coupled to the most different types of instrument, where these only require the corresponding connecting locations for the adapter. Various instruments can now be coupled to an adapter during an operation or decoupled therefrom, which is very simple, does not require great concentration and is also very fast. Should the position of the distal end be detected, then the only necessary information when changing the instrument is how far the tip is removed from the adapter, which can be determined by the CAS system itself through corresponding input data and memory data in the processor unit or through corresponding instrument specifications.

The provision of this adapter now opens the possibility of separating at a defined location sterile portions of the medical instrument system, for example an endoscope, from non-sterile portions, for example a camera with connecting cables to monitors in the operating room. One only needs to adjust the adapter with its transmitter unit to the detection system of the CAS system, and then any properly configured instruments can be coupled to the adapter.

This considerably increases the flexibility in such operations and at the same time simplifies the operation of the CAS system with the corresponding array of instruments.

In a preferred embodiment of the invention, the adapter comprises at least one further reception coupling, with which it can be coupled to a further medical instrument. The feature has the advantage that the adapter including the transmitter unit can be employed at a favorable, intermediate position within the instrument system. Favorable means that the position is favorable for detection of the transmitter location of the transmitter unit and/or a favorable ergonomic arrangement without disturbing the operator.

In a further embodiment of the invention, the adapter is configured such that on a first side, it can be coupled to a proximal end of an instrument whose position is to be detected through the transmitter unit. The feature has the advantage that the adapter is coupled at an easily accessible location, where the instrument is not disturbed in its handling capabilities. To exchange the instrument, the connection is simply released and another instrument is coupled to the adapter at its proximal end.

In a further embodiment of the invention, the adapter at a second side is formed as the proximal end of the instrument, which can be coupled to the first side of the adapter. This has the considerable advantage that no constructive alterations of the components are necessary, for example a camera, which normally is directly connected to the instrument, for example an endoscope.

It is also possible to still use existing or standardized components and the present adapter need only be connected therebetween. This not only simplifies the CAS system, but is also very inexpensive.

In a further embodiment of the invention, the adapter comprises a reception coupling on its first side for coupling to an ocular cup. In this form, the adapter is suited for simple connection to the most often used instrument in endoscopic operations, namely an endoscope. The adapter can be simply coupled to existing, common endoscope systems because endoscopes of different types from one manufacturer or from several manufacturers usually have standardized ocular cups. An ocular cup offers a relatively large, approximately ring-shaped coupling surface, so that the adapter can be simply and securely attached and a very exact position detection is possible when coupled to various models of endoscopes.

In a further embodiment of the invention, the adapter comprises a reception coupling on its second side in the form of an endoscope ocular cup. The feature has the considerable advantage that the adapter on the second side is formed as the mentioned standardized ocular cup, and therefore can be simply coupled to the corresponding standardized coupling location on cameras. Here again, the ocular cup geometry allows a relatively large and geometrically favorable attachment surface, namely in circular form. Thus a particularly simple, rapid and exactly fitting can be made on this side with the further components, so that the adapter on the whole and thus the transmitter unit is integrated in exact position in the endoscopic system.

Embodiments are also possible in which the actual ocular cup is much smaller than the standard ocular cup as is common in pure video endoscopy.

In a further embodiment of the invention, the adapter is configured such that image transmission is possible between the coupling locations where the adapter connects the two components of the endoscopic system. This feature has the considerable advantage that the intermediate adapter makes image transmission possible, if the instrument is an endoscope, and the image is not negatively influenced or disturbed. The adapter thus also fulfills a further function, namely it enhances undisturbed and exact image transmission.

Further optical elements, particularly imaging elements or filters can be arranged in the adapter in advantageous manner.

In a further embodiment of the invention, an optical window is arranged between the coupling locations of the adapter, so that one coupling location can be hermetically separated from the other coupling location.

This feature has the considerable advantage that the adapter with the optical window serves as a separator, for example between the sterile instrument and the non-sterile camera, that it is ensured at the same time that an image can be transmitted when the instrument is an endoscope, and that it is ensured that despite several exchanges of the instrument during an operation, the two instruments coupled by the adapter are hermetically separate from one another, so that no contamination can be transmitted from one to the other. This contributes not only to simple handling but also to hygienically safe operation of the endoscopic system.

In a further embodiment of the invention, the reception coupling for connection of the instrument to be detected is configured to be self-centering. The feature has the advantage that when exchanging the instrument, the operator need not pay close attention to the exchange and connection steps, but only need to place the instrument on the corresponding coupling location of the adapter and for example apply pressure or push the instrument. The coupling itself takes care of the centering. This is particularly favorable for image transmission because the optical axis of the instrument then exactly corresponds to the optical axis of the adapter.

In a further embodiment of the invention, the position errors caused by the dimensional tolerances of the reception coupling following the coupling procedure are small. The feature has the advantage that the position detection error caused by the tolerances is extremely small. In particular, exactly fitted connections without large radial or axial play can be achieved with the above-mentioned geometries, i.e. the round ocular cuplike coupling locations, while it is still ensured that easily accessible and simple coupling procedures can be carried out.

In a further embodiment of the invention, the position errors of the reception couplings are reproducible. This feature has the advantage that corresponding computer defined corrections can be made on the basis of these reproducible deviations, where the deviations are accounted for in the total measurement accuracy of the CAS system.

In a further embodiment of the invention, the reception coupling for connecting an instrument is configured such that the two components can only be coupled to one another in a certain relative position. In some instruments, for example endoscopes with a side view, the distal end piece is not exactly perpendicular to the center axis of the endoscope shaft, but inclined thereto. This means that images are taken from sites which are closer or further away from the proximal end of the endoscope. It is then desirable that the endoscope be coupled in a single particular angular position relative to the adapter or to the camera attached thereto, which is easy to accomplish with corresponding orientation elements on the adapter.

In a further embodiment of the invention, the transmitter unit is attached to the adapter such that its transmitter is arranged in a direction transverse to the longitudinal axis of the instrument. The feature has the advantage that all transmitters have about the same distance to the tip of the instrument, so that inherent system errors influencing the length of the distance are about equal and thus can also be computationally suppressed or eliminated. The localization error increases with increasing distance between the position to be localized, i.e. the tip of the instrument, and the transmitters. Thus the arrangement of the transmitter unit transversely on the adapter, which is attached at the proximal end of the instrument, provides a good solution because this distance is not so large and at the same time, the freedom in handling the instrument is not impaired by the adapter with its transmitter unit. For example, the entire length of the endoscope shaft remains unhindered by the adapter. This configuration is ergonomic and saves space.

In a further embodiment of the invention, the transmitter unit is approximately bar-shaped and extends in transverse direction to the optical axis of the adapter. The feature has the advantage that the transmitter unit is formed in compact construction and the handling of the adapter is simplified. The configuration is particularly ergonomic and especially favorable with respect to the construction length.

In a further embodiment of the invention, the transmitter unit is arranged such that its transmitters lie along the longitudinal axis of the instrument. The feature has the advantage that the basic lengths for determining the tip of the instrument are relatively long and therefore the measurement error is small. The accuracy of determining the angular position about the instrument axis is then smaller, but the angular position as such is often less accurate to detect. A distribution along the instrument axis leads to a slender construction and the view along the longitudinal axis is less hindered.

In a further embodiment of the invention, the transmitters of the transmitter unit are distributed on a surface. The feature has the advantage that the highest possible accuracy of position detection is possible.

In a further embodiment of the invention, the transmitter unit comprises transmitters known per se which send out ultrasound, IR or other electromagnetic radiation. This feature has the advantage that a contactless detection of position can take place via radiation or fields emitted by the transmitters to cameras or other suitable sensors in the operation room.

In a further embodiment of the invention, the transmitter unit comprises transmitters including passively reflecting elements or transmitters which can be activated by radiation. The feature has the advantage that the passively reflecting elements do not require an energy supply which strongly influences the constructive design of the adapter. Actively radiating transmitters require either an energy source in the form of batteries or a cable connection to an external energy source, which is disturbing. Radiation-activated transmitters, for example configured as transponders also do not require their own energy supply.

It will be understood that the above-mentioned features and those to be discussed below are not only applicable in the given combinations but may be employed in other combinations or taken alone without departing from the scope of the present invention.

BRIEF DESCRIPTION OF THE DRAWINGS

The invention will be described and discussed in the following in conjunction with a selected embodiment.

DETAILED DESCRIPTION OF PREFERRED EMBODIMENTS

Figure 1:
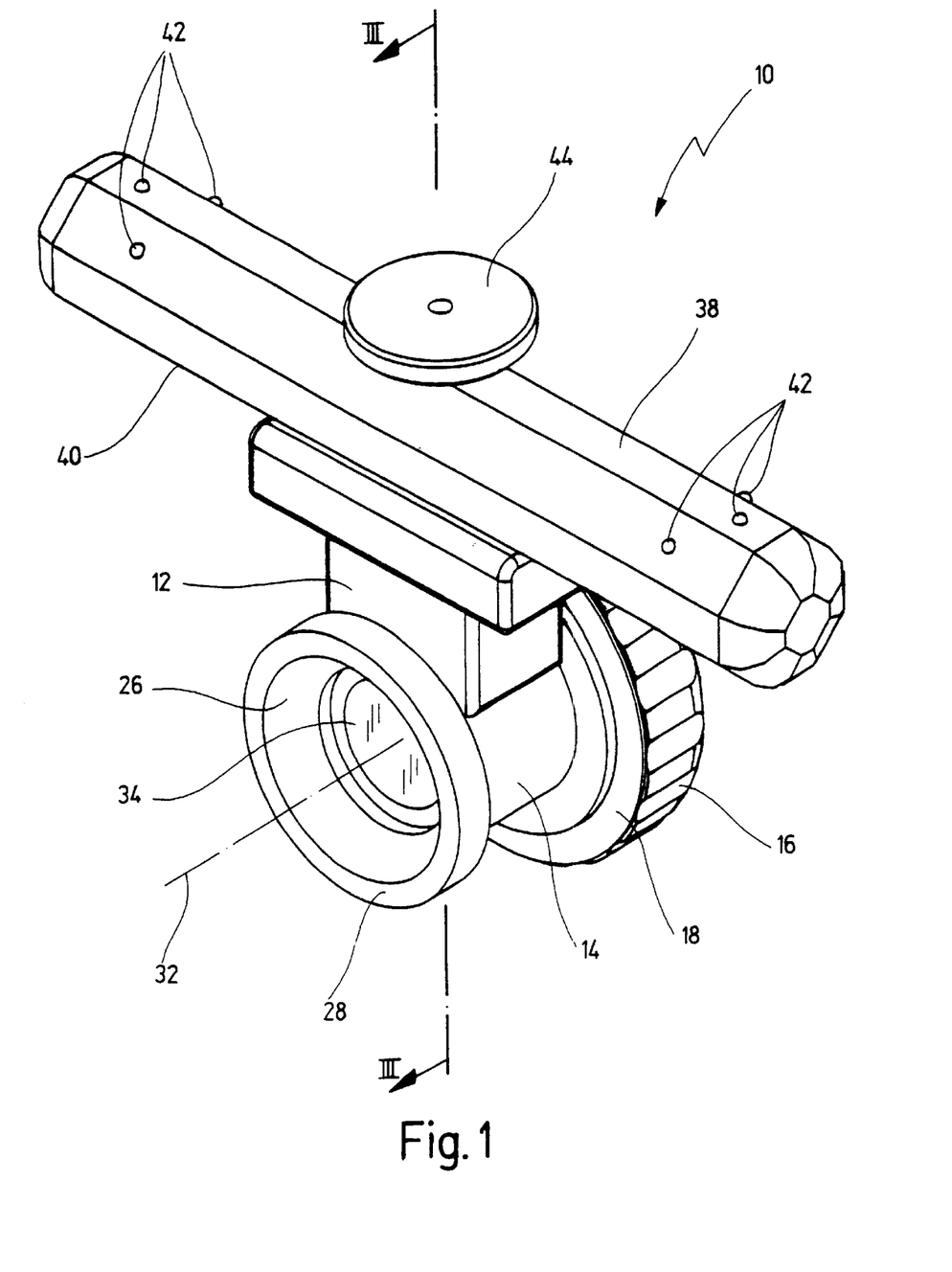
FIG. 1 shows a perspective view of an adapter, where one coupling location for coupling to a camera is recognizable.
Figure 2:
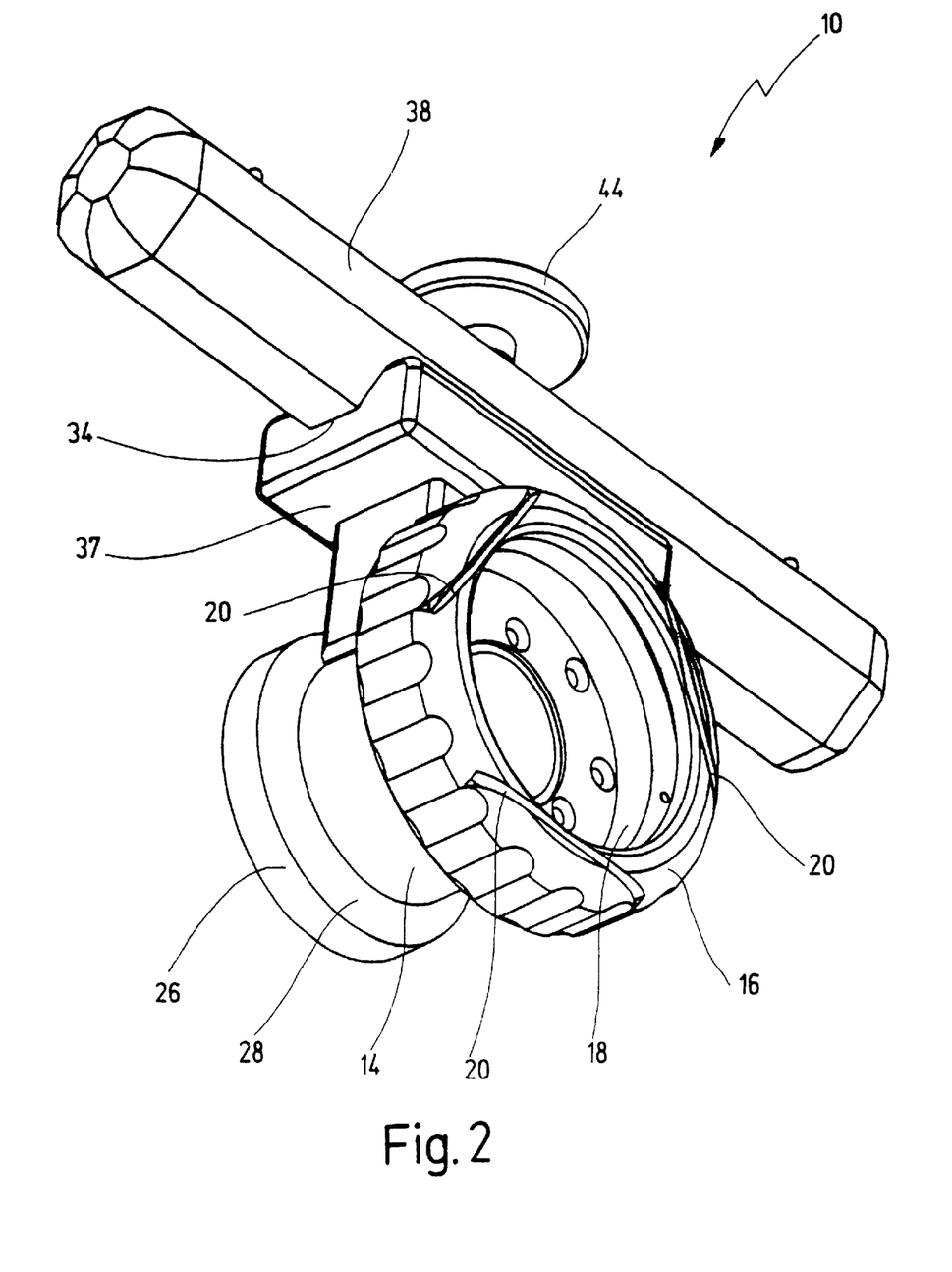
FIG. 2 shows another perspective view of the adapter of FIG. 1, where the opposite coupling location for coupling with an instrument is recognizable.
Figure 3:
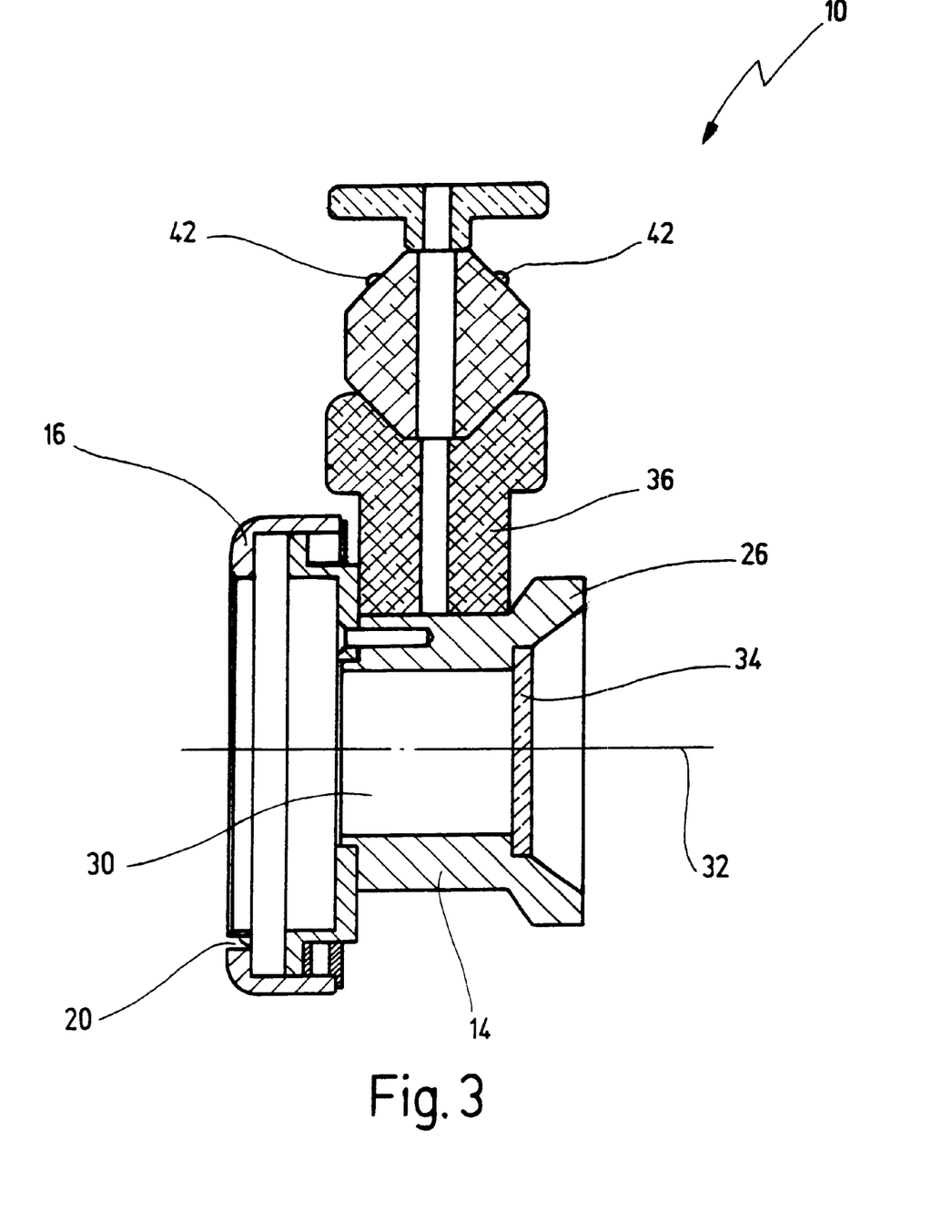
FIG. 3 shows a cross-section along the line III—III in FIG. 1.

An apparatus as shown in FIGS. 1 to 3 with a transmitter unit, with which the position of a medical instrument can be detected with a CAS system, is designated generally with the numeral 10. The apparatus 10 is formed as an adapter 12 having a central hollow cylindrical body 14. A reception coupling 16 is provided at one end of the hollow cylindrical body.

The reception coupling 16 is formed as a ring 18 having a securement well not described in detail here. Three cut-outs 20 uniformly displaced about the circumference running along secants of the outer circle are cut into the ring. These cut-outs provide a certain flexibility, so that an ocular cup 22 of an endoscope 24 can be inserted into the ring, which can best be seen in the illustrations of FIGS. 4 and 5.

The reception coupling 16 thus serves to couple the proximal end of an endoscope 24 with its ocular cup 22 onto the adapter 12, i.e. onto the annular ring surface. When the ocular cup 22 is inserted, the circumferentially uniformly distributed cut-outs 20 or the resulting movable parts of the ring 18 produce an exact centering of the ocular cup 22 in the reception coupling 16.

The hollow cylindrical body 14 of the adapter 12 comprises a further reception coupling 26 at the end opposing the reception coupling 16, which has the form of an ocular cup 28. The form of the ocular cup 28 here corresponds to the ocular cup 22 which can be inserted into the reception coupling 16.

As can be seen in the cross-sectional illustration of FIG. 3, a continuous optical path 30 is located in the interior of the adapter, whose optical axis 32 also represents the center axis of the hollow cylindrical body 14. An optical window 34 is fitted into a region of the reception coupling 26, which hermetically separates the path 30. Said in another way, it is not possible for contamination, for example from a system component such as an endoscopic camera connected to the reception coupling 26, to be transmitted by the inner path 30 to the other instrument connected to reception coupling 16, for example an endoscope 24. It will be understood that this also holds for the reverse situation. Image transmission however is still possible despite the hermetic separation by the optical window 34.

A radially projecting attachment 36 is attached to the outer side of the hollow cylindrical body 14 of the adapter 12, whose outer end is provided with a recess 37 for receiving a transmitter unit 38.

The transmitter unit 38 is formed as a bar 40 whose longitudinal axis is disposed transversely or perpendicular to the optical axis 32. In a further embodiment (not shown) the bar 40 is rotated by 90° and extends in the direction of the optical axis 32.

Three transmitters 42 are arranged and distributed over a surface on the bar 40 at each of the opposing ends, namely such that the three transmitters in each case lie at the corners of a triangle. The purpose of this arrangement will be described below in conjunction with FIG. 5 and the operation of the CAS system.

A screw 44 serves to secure and to exchange the transmitter unit 38 on the attachment 36. The relative position between the transmitter unit 38 and the adapter 12 is definitively defined and secured by this connection.

Figure 4:
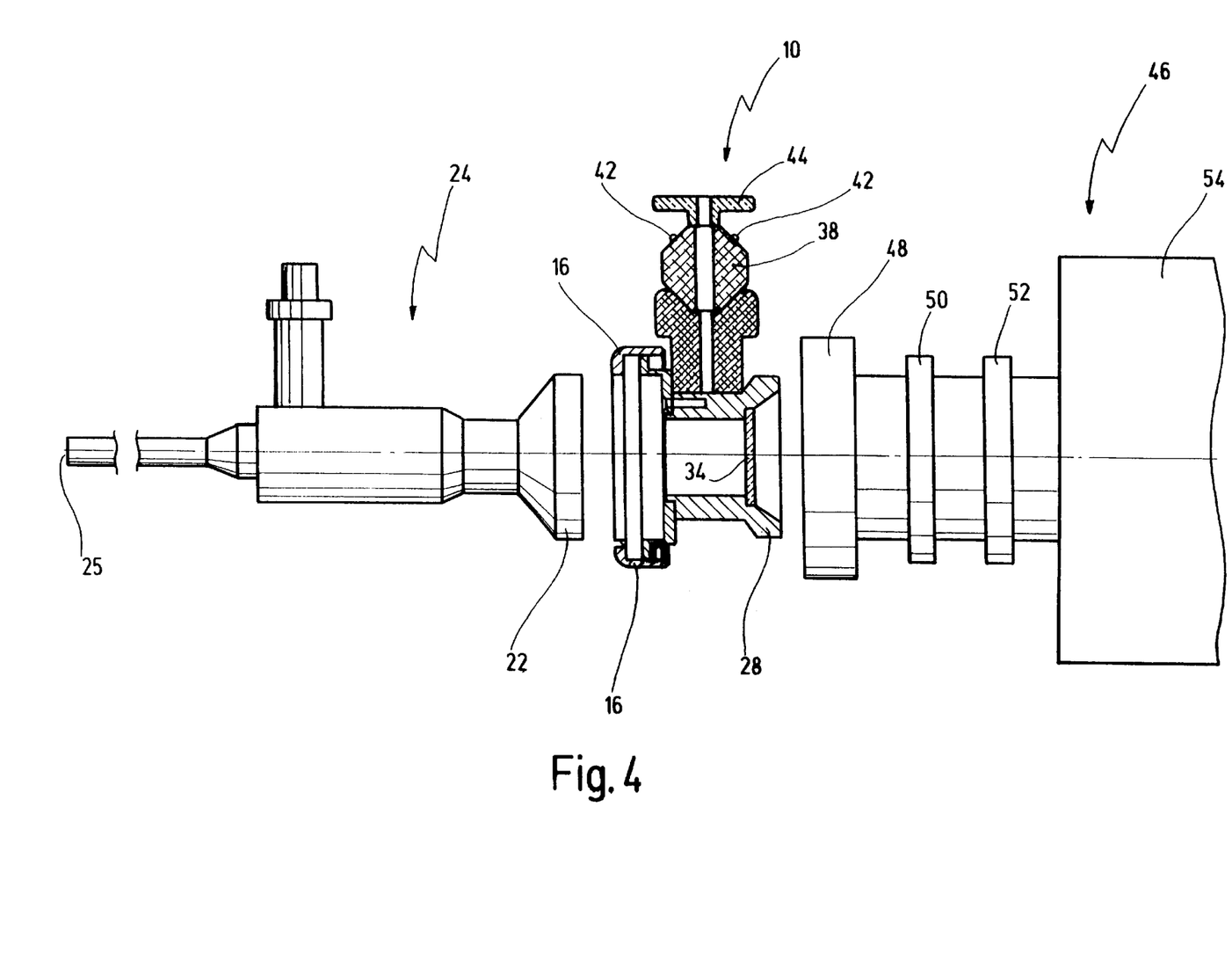
FIG. 4 shows a partial cross-sectional representation of two components to be coupled at opposite ends of the adapter in FIGS. 1 to 3, namely an endoscope on one side and a camera on the opposite side.

As mentioned above, the reception coupling 16 serves to connect an endoscope 24 as seen in the illustration of FIG. 4. The reception coupling 26 is provided to allow connection with a camera 46. The camera 46 has a coupling 48 which can be passed over the reception coupling 26 formed as an ocular cup 28 of the adapter 12 and can be locked with elements known per se. The coupling 48 is formed as a standard coupling and normally provides a connection of the camera 46 directly with an ocular cup 22 of an endoscope 24. Therefore, the reception coupling 26 is formed as a corresponding ocular cup 28.

Figure 5:
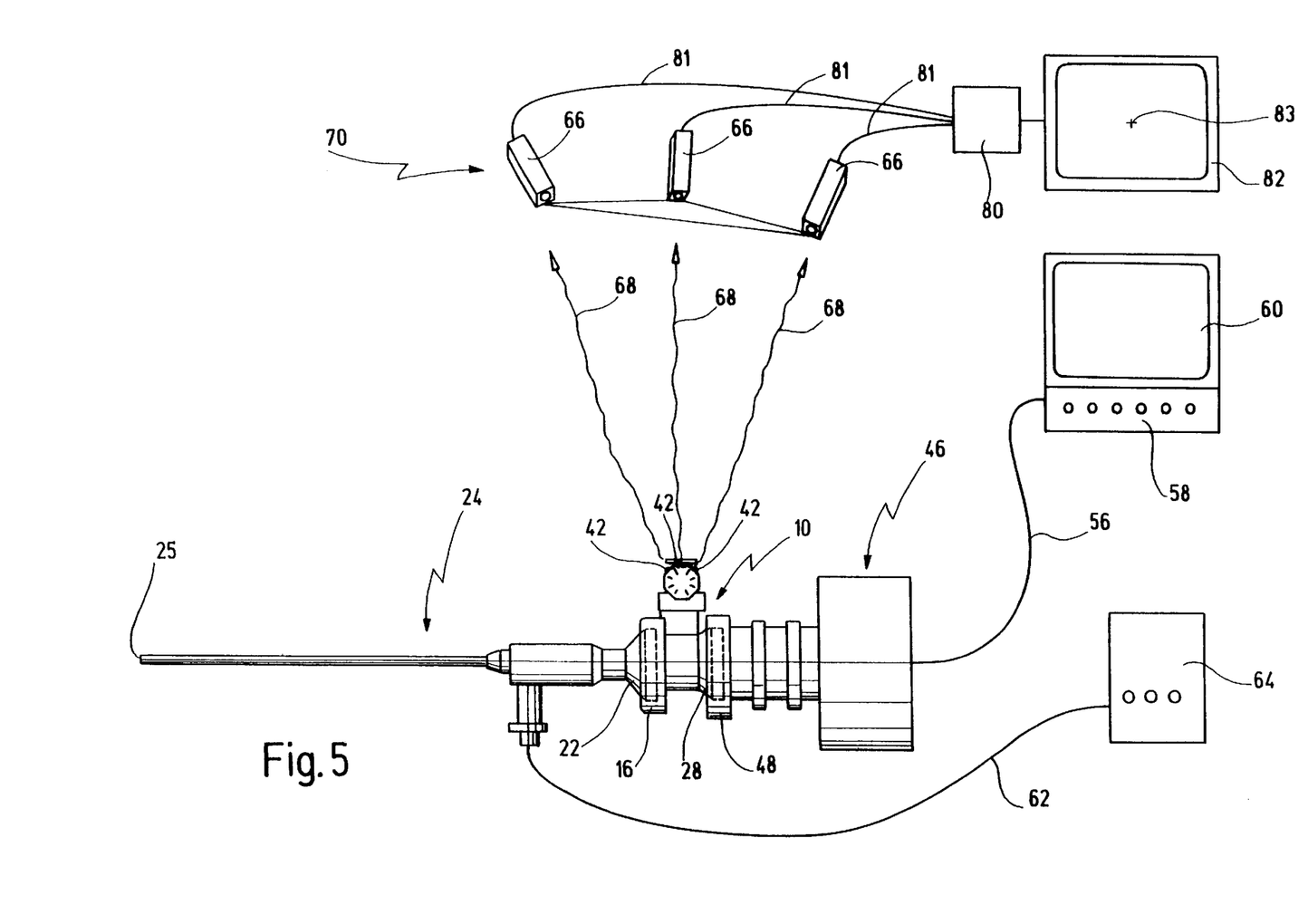
FIG. 5 shows a highly schematic illustration of a CAS system together with an endoscopic operation system in which the adapter of FIGS. 1 to 4 is arranged between the components, endoscope and camera.

The camera 46 further comprises a focus ring 50 and a zoom 52, where these elements project from the actual camera body 54. To connect the adapter 12 with the two components endoscope 24 and camera 46, these are coupled to one another as described above. FIG. 5 shows this condition, i.e. the ocular cup 22 of the endoscope 24 is inserted into the reception coupling 16, while the coupling 48 of the camera 46 is passed over the reception coupling 26 formed as an ocular cup 28. The adapter therefore sits in a defined position and is fixed between the two components, namely the endoscope 24 and the camera 46.

The camera 46 is connected to a video processor 58 via a cable 56 and in turn with an endoscope monitor 60. The monitor 60 displays the image visible through the endoscope 24. The endoscope 24 is connected with a light source 62 via an optical fibre cable 62. This assembly represents an endoscopic system. At least two, preferably three, IR cameras 66 are arranged in the room in which the assembly including the adapter 12, endoscope 24 and the camera 46 is to be employed, for example in an operation room, which detect the IR radiation emitted by the transmitters 42.

The absolute position of the assembly can be determined by the IR cameras 66 because the transmitters 42 as mentioned are arranged at the points of a triangle, thus defining a certain plane. This data is then supplied to a CAS computer 80, which is connected to the IR cameras 66 by the lines 81 and the data is processed along with data on the position of the tip 25 of the endoscope 24 relative to the transmitter unit 38. With this, the position of the tip 25 of the endoscope 24 can be definitively determined.

In corresponding manner, the position of a patient is determined in a reference measurement and this data is also supplied to the CAS computer 80. The CAS computer 80 is an image processing system in which the anatomical data of a patient is present in the form of CT or MR images.

Thus it is now possible to display the position of the tip 25 of the endoscope on the CAS monitor 82 with reference to the CT or MR data, for example in the form of a marking 83, so that the operator can orient himself exactly on the basis of the image on the CAS monitor 82.

The endoscope monitor 60 and the CAS monitor 82 can also be identical with one another, where the endoscope and the CAS image can be displayed alternately or simultaneously by switching or separating the images on the screen.

Position detections can be continuously carried out by the prominent position of the transmitter unit 38, so that the mentioned technique of computer assisted surgery can be carried out. The largely schematic illustration of the system in FIG. 5 represents a so-called CAS (computer assisted surgery) system 70.

In the above-described embodiment, the adapter 12 contains an optical window 34. Operations are conceivable in which the adapter 12 is only coupled to the ocular cup 22 of an endoscope 24 and no camera 46 is present, but the operation area is visible through the endoscope or is observed through the attached adapter 12. In this case, the optical window 34 is not necessary. Should the endoscope be configured such that further channels for instruments are provided, these instruments can be passed through the hollow cylindrical body 14 of the adapter into the endoscope and the corresponding manipulations can be carried out.

However, since the endoscope 24 must first be placed at a site, this procedure can evidently be carried out with a CAS system as described above, which determines the position of the assembly composed of the endoscope 24 and the adapter 12 as well as the position of the transmitters 42.

Surgical instruments can then also be coupled to the adapter of the present invention, if their end piece is formed as an ocular cup. This holds for example when a trocar with an obturator is to be guided to the operation site without visual control. The CAS system allows the continuous monitoring of the position reached. In this case, the optical transmission capability and the possibility of coupling at the proximal side of the adapter are not made use of.

As described above, the exact position of the tip 25 of the endoscope 24 is to be determined. It is also possible to precisely detect a certain location displaced from the tip 25, for example a location a few centimeters from the tip. This location is of interest because in an endoscopic operation, the location directly at the tip is not of primary interest, but a location a few centimeters from the tip, namely at the location where the actual operative measure is carried out. This location can be made visible for the operator in that two laser beams are transmitted through the optical fiber in the endoscope, for example lying diametrically opposite. The exiting light is then such that these two beams cross one another a few centimeters before the tip and produce a light spot clearly visible to the operator, which corresponds precisely to the location which should actually be observed. The CAS system can then display this site of the "elongate" endoscope in the 3D data set and the operator can direct the crossing point of the two laser beams in his view to the tissue of interest.

What is claimed is:

1. An adapter for coupling with an endoscope and at least one other medical instrument comprising an adapter body a first coupling provided on one side of said adapter body for coupling said adapter releasable, but mechanically fixed and in a simple manner to a predetermined coupling location on an endoscope, a second coupling provided on another side of said adapter body for coupling with a medical instrument, said adapter body is provided with a transmitter unit, via which transmitter unit a position of an endoscope coupled to said adapter can be detected by a CAS (Computer Assisted Surgery)-system, said transmitter unit comprising several transmitters distributed on said transmitter unit, a respective position of each transmitter is detectable by said CAS-system.

2. Adapter of claim 1, wherein said adapter is configured such that it can be coupled on said one side of said adapter body to a proximal end of said endoscope whose position is to be detected by said transmitter unit.

3. Adapter of claim 2, wherein said proximal end of said endoscope is an ocular cup.

4. Adapter of claim 1, wherein said adapter is configured on said other side of said adapter body as a proximal end of said endoscope coupled on said one side of said adapter body.

5. Adapter of claim 3, wherein said proximal end of said endoscope is an ocular cup.

6. Adapter of claim 1, wherein said adapter body is configured such that an image can be transmitted between said first coupling and said second coupling when coupled with an endoscope and a medical instrument being part of an endoscopic system.

7. Adapter of claim 6, wherein an optical window is arranged between said first coupling and said second coupling thereby hermetically separating said first coupling from said second coupling.

8. Adapter of claim 1, wherein optical elements are arranged within said adapter body between said first coupling and said second coupling.

9. Adapter of claim 8, wherein said optical elements are selected from the group consisting of imaging elements and filters.

10. Adapter of claim 1, wherein said first coupling is designed in that when coupling said endoscope, this endoscope is self-centered within said first coupling.

11. Adapter of claim 1, wherein position errors caused by dimensional tolerances of said first coupling and said second coupling, respectively, when having coupled an endoscope or other medical instrument thereon are small.

12. Adapter of claim 11, wherein said position errors of said couplings are reproducible.

13. Adapter of claim 1, wherein said endoscope can be coupled with said first coupling in a predetermined relative position one to another only.

14. Adapter of claim 1, wherein said transmitter unit is attached to said adapter body such that its transmitters are arranged in a direction traverse to a longitudinal axis of said endoscope.

15. Adapter of claim 14, wherein said transmitter unit is bar-shaped and extends transversely to an optical axis of said adapter.

16. Adapter of claim 1, wherein said transmitter unit is arranged such that its transmitters lie along a longitudinal axis of said endoscope.

17. Adapter of claim 1, wherein said transmitters of said transmitter unit are arranged to be distributed over a surface of said transmitter unit.

18. Adapter of claim 1, wherein said transmitters transmits ultrasound.

19. Adapter of claim 1, wherein said transmitters transmit electromagnetic radiation.

20. Adapter of claim 19, wherein said electromagnetic radiation is IR-radiation.

21. Adapter of claim 1, wherein said transmitter unit comprises transmitters which are passively reflecting elements.

22. Adapter of claim 1, wherein said transmitter unit comprises transmitters which are activated for transmitting by radiation of said CAS-system.

23. An adapter for coupling with at least two medical instruments comprising an adapter body a first coupling provided on one side of said adapter body for coupling said adapter releasable, but mechanically fixed and in a simple manner to a predetermined coupling location on a first medical instrument, a second coupling provided on another side of said adapter body for coupling with a second medical instrument, said adapter body is provided with a transmitter unit, via which transmitter unit a position of a medical instrument coupled to said adapter can be detected by a CAS (Computer Assisted Surgery)-system, said transmitter unit comprising several transmitters distributed on said transmitter unit, a respective position of each transmitter is detectable by said CAS-system, wherein said adapter body is configured such that an image can be transmitted between said first coupling and said second coupling when coupled with two medical instruments being part of an endoscopic system.

24. Adapter of claim 23, wherein an optical window is arranged between said first coupling and said second coupling thereby hermetically separating said first coupling from said second coupling.

25. An adapter for coupling with at least two medical instruments comprising an adapter body a first coupling provided on one side of said adapter body for coupling said adapter releasable, but mechanically fixed and in a simple manner to a predetermined coupling location on a first medical instrument, a second coupling provided on another side of said adapter body for coupling with a second medical instrument, said adapter body is provided with a transmitter unit, via which transmitter unit a position of a medical instrument coupled to said adapter can be detected by a CAS (Computer Assisted Surgery)-system, said transmitter unit comprising several transmitters distributed on said transmitter unit, a respective position of each transmitter is detectable by said CAS-system, wherein optical elements are arranged within said adapter body between said first coupling and said second coupling.

26. Adapter of claim 25, wherein said optical elements are selected from the group consisting of imaging elements and filters.

* * * * *